(12) United States Patent
Rosso et al.

(10) Patent No.: US 8,809,592 B2
(45) Date of Patent: Aug. 19, 2014

(54) PROCESS FOR PRODUCING DIBK

(75) Inventors: Giovanni Rosso, Sao Paulo (BR);
Wilson Martins, Sao Paulo (BR)

(73) Assignee: Rhodia Poliamida e Especialidades Ltda, Sao Paulo (BR)

( * ) Notice: Subject to any disclaimer, the term of this patent is extended or adjusted under 35 U.S.C. 154(b) by 0 days.

(21) Appl. No.: 13/990,695

(22) PCT Filed: Nov. 17, 2011

(86) PCT No.: PCT/IB2011/002728
§ 371 (c)(1),
(2), (4) Date: May 30, 2013

(87) PCT Pub. No.: WO2012/073082
PCT Pub. Date: Jun. 7, 2012

(65) Prior Publication Data
US 2013/0245326 A1    Sep. 19, 2013

(30) Foreign Application Priority Data
Nov. 30, 2010  (FR) ..................... 10 59895

(51) Int. Cl.
*C07C 45/66* (2006.01)
(52) U.S. Cl.
USPC ....................................... 568/392

(58) Field of Classification Search
USPC .......................................... 568/392
See application file for complete search history.

(56) References Cited

U.S. PATENT DOCUMENTS

| 6,008,416 A | 12/1999 | Lawson et al. |
| 2003/0139629 A1 | 7/2003 | Vandersall et al. |

FOREIGN PATENT DOCUMENTS

JP    61-005038 A1    1/1986

OTHER PUBLICATIONS

Seki et al, "Palladium Supported on an Acidic Resin: A Unique Bifunctional Catalyst for the Continuous Catalytic Hydrogenation of Organic Compounds in Supercritical Carbon Dioxide," Adv. Synth. Catal., 2008, pp. 691-705, vol. 350.
Yng-Long et al, "Ketones," Encyclopedia of Chemical Technology, 2001, pp. 1-47, vol. 14.
International Search Report issued on Mar. 13, 2012, by the European Patent Office as the International Searching Authority in corresponding International Patent Application No. PCT/IB2011/002728.
Written Opinion of the International Searching Authority issued on Mar. 13, 2012, in corresponding International Patent Application No. PCT/IB2011/002728.

*Primary Examiner* — Sikarl Witherspoon
(74) *Attorney, Agent, or Firm* — Dentons US LLP

(57) ABSTRACT

A process for producing diisobutyl ketone (DIBK) which includes bringing together triacetone dialcohol (TDA) and a bifunctional catalyst that can perform a dehydration and hydrogenation reaction is described.

18 Claims, No Drawings

PROCESS FOR PRODUCING DIBK

CROSS-REFERENCE TO PRIOR APPLICATIONS

This application is a National Stage of PCT/IB2011/002728, filed Nov.17, 2011, and designating the United States (published in French on Jun.7, 2012, as WO 2012/073082 A1), which claims priority under 35 U.S.C. §119 to FR 10 59895, filed Nov. 30, 2010, each hereby expressly incorporated by reference in its entirety and each assigned to the assignee hereof.

The present invention relates to a process for the production of diisobutyl ketone (DIBK) which consists in bringing together triacetone dialcohol (TDA) and a bifunctional catalyst capable of carrying out a dehydration and hydrogenation reaction.

PRIOR ART

Diisobutyl ketone (DIBK) is a compound used in many industrial applications. It is used in particular as solvent for certain polymers, such as nitrocellulose and epoxy resins. It can be used for coatings, paints and inks, in particular. It is also used as extraction solvent in the pharmaceutical industry.

DIBK is generally produced at the same time as methyl isobutyl ketone (MIBK) in a condensation reaction of acetone. However, the conversion and the selectivity for DIBK are very low and wholly insufficient.

INVENTION

The Applicant Company has just demonstrated a novel process for the production of diisobutyl ketone (DIBK), in which triacetone dialcohol (TDA) and a bifunctional catalyst capable of carrying out a dehydration and hydrogenation reaction are brought at least together. This process makes it possible to obtain DIBK with an excellent conversion and an excellent selectivity.

A bifunctional catalyst is a type of catalyst which is well-known in chemistry and which is capable of catalyzing two types of reaction, also known as dual function catalyst. The bifunctional catalyst of the invention makes the dehydration possible in acidic or basic media and makes the hydrogenation possible in particular in the presence of a metal supported on the catalyst.

It is preferable in particular to carry out a dehydration in an acidic medium aided by a high temperature.

The bifunctional catalyst comprises, as first component, an acidic or basic solid compound. This compound can be an organic or inorganic solid of the alumina, zeolite, clay, ceramic, phosphate or resin type. Mention may in particular be made, as acidic solid support, of sulfonic acid resins, carboxylic resins, phosphoric resins, inorganic oxides, such as sulfated zirconias, acidic clays, such as montmorillonites, and zeolites, such as H—ZSM5 and H—Y. Mention may be made, as basic solid support, of the compounds carrying, at the surface, hydroxide functional groups or amine functional groups, carbonates, metal oxides, such as lanthanum phosphates or oxides, or basic clays, such as lamellar double hydroxides (LDHs).

The catalytic system comprises, as second component, a metal, alkali metal or alkaline earth metal compound A. Mention may in particular be made, as metal component, of those based on Cr, Co, Ni, Cu, Rh, Pd, Ir, Pt, Mo, W, Zn, P, As, Sb, Si, Ge, Sn, Al, Ga, Ti, Zr, Hf and/or Au. Mention may in particular be made, as alkali metal or alkaline earth metal component, of those based on Li, Na, K, Rb, Cs, Be, Mg, Ca and/or Sr. Preference is given in particular to Ni, Pd, Rh and Ir. This compound can be used as is or in the hydroxide, oxide or salt form. The metal is preferably in the reduced state for its activity during the hydrogenation.

The bifunctional catalyst preferably comprises a metal compound based on Cr, Co, Ni, Cu, Rh, Pd, Ir, Pt and/or Au.

The metals of the platinum group, in particular platinum, palladium, rhodium and ruthenium, are catalysts which are particularly active and which act at low temperature and low $H_2$ pressure.

These catalysts are described in particular in the application US2003/0139629, the patent U.S. Pat. No. 6,008,416 and the publication <<*Pd supported on an Acidic resin . . .* >>, Seki et al., Adv. Synth. Catal., 2008, 350, 691-705.

Use may in particular be made of the metal, alkali metal or alkaline earth metal compound A in proportions of between 0.001% and 30% by weight, more preferably between 0.01% and 10% by weight, with respect to the weight of the acidic or basic solid compound.

According to a preferred subject matter of the invention, the catalytic system comprises an acidic or basic solid compound on which the compound A described above is supported at the surface. Mention may be made, for example, of the Amberlyst(R) CH28 catalysts. It is also possible for the catalytic system to comprise an acidic or basic solid compound and a compound A supported on a solid which is inert with regard to the reaction.

The catalyst can be placed on a fixed bed or else can be suspended with stirring in the reactor.

The proportion of catalyst can vary between 0.01% and 60% by weight, with respect to the weight of the TDA, preferably between 0.1% and 20% by weight, more preferably between 1% and 10% by weight.

The reaction medium comprises in particular TDA and optionally other compounds, such as one or more solvents, for example.

The reaction medium can optionally comprise one or more solvents, such as polar or nonpolar and protic or aprotic solvents, particularly polar protic solvents, polar aprotic solvents and nonpolar aprotic solvents. Preference is given in particular to alcohols, such as methanol, ethanol and isopropanol.

The reaction medium preferably comprises from 30 to 70% by weight of TDA and from 30 to 70% by weight of DAA, more particularly from 40 to 60% by weight of TDA and from 40 to 60% by weight of DAA.

In that case, the manufacture is thus carried out of DIBK from TDA and of MIBK from DAA.

The present invention thus also relates to a process for the production of DIBK and MIBK by bringing TDA and DAA together with the bifunctional catalyst of the present invention.

The reaction medium can result directly or indirectly from a unit for the production of DAA; more specifically, from the bottom of the distillation column of a unit for the production of DAA, successively to the catalyzed condensation of the acetone. It is perfectly possible to increase the concentration of TDA in the medium resulting from a unit for the production of DAA or to remove certain impurities, for example by distillation or crystallization.

Preferentially, the reaction is carried out at a temperature of between 10° C. and 200° C., more preferably between 30° C. and 150° C. It is observed in particular that the dehydration of the TDA is increased by the synergistic effect of the acid catalysis of the bifunctional catalyst and the high temperatures.

Preferentially, the reaction is carried out at a pressure of between 1 and 100 bar, more preferably between 3 and 25 bar and more preferably still between 8 and 15 bar. Such a pressure can be obtained by feed addition to the reactor of pure hydrogen or of a mixture of hydrogen and an inert gas, such as, for example, nitrogen or argon. The hydrogen partial pressure can be maintained by bleeding the gas headspace while monitoring the hydrogen content.

The process according to the invention can be carried out continuously or batchwise, preferably in the liquid phase. The residence time of the reaction can in particular be from 5 to 300 minutes.

The reaction can be carried out in a reactor of any type, in particular in a vertically mounted reaction tube. Several reactors carrying out the process of the invention can be placed in series.

It is preferable in particular to introduce, into a reactor, triacetone dialcool (TDA) and to bring it together with a bifunctional catalyst capable of carrying out a dehydration and hydrogenation reaction and to subsequently initiate the reaction for the synthesis of diisobutyl ketone (DIBK). It is possible in particular to initiate the reaction by pressurization, in particular with hydrogen, and/or placing at temperature.

It is possible to carry out one or more stages of purification, in particular by distillation, of the product obtained after the reaction stage, for example in order to recover the reactant or reactants.

A specific language is used in the description so as to facilitate understanding of the principle of the invention. Nevertheless, it should be understood that no limitation of the scope of the invention is envisioned by the use of this specific language. Modifications and improvements can in particular be envisaged by a person conversant with the technical field concerned on the basis of his own general knowledge.

The term "and/or" includes the meanings "and" and "or" and all the other possible combinations of elements connected with this term.

Other details or advantages of the invention will become more clearly apparent in the light of the examples given below purely by way of indication.

EXPERIMENTAL SECTION

Example 1

Batchwise Reaction

A charge of 7.01 g of acidic solid catalyst based on sulfonic resin comprising palladium and of 70.05 g of a mixture comprising 50% by weight of TDA and 50% by weight of DAA is produced in a stirred 100 ml reactor. Subsequently, the device is closed, pressurized with hydrogen and heated up to a temperature of 120° C. and a pressure of 10 bar, for a period of time of 4 hours. At the end of the reaction, the conversion of the TDA reaches 100% and the selectivity of the TDA for DIBK is 85%.

Furthermore, the presence of MIBK is observed. At the end of the reaction, the conversion of the DAA reaches 100% and the selectivity of the DAA for MIBK is 92%.

The selectivity of a chemical reaction specifies the amount of desired product formed with respect to the number of moles of the limiting reactant consumed. It indicates if several reactions are taking place in parallel, resulting in undesired byproducts, or if the desired reaction is the only one to consume reactant. An excellent selectivity for DIBK is thus observed in the context of the process of the present invention.

Example 2

Comparison

A charge of 7.01 g of acidic solid catalyst based on sulfonic resin comprising palladium and of 70.04 g of acetone is produced in a stirred 100 ml reactor. Subsequently, the device is closed, pressurized with hydrogen and heated up to a temperature of 120° C. and a pressure of 10 bar, for a period of time of 3 hours. At the end of the reaction, the conversion reaches 64% and the selectivity for DIBK is only 3%.

The invention claimed is:

1. A process for the production of diisobutyl ketone (DIBK), the process comprising bringing together at least triacetone dialcohol (TDA) and a bifunctional catalyst that can carry out a dehydration and hydrogenation reaction.

2. The process as defined by claim 1, wherein the bifunctional catalyst comprises an acidic or basic solid compound selected from the group consisting of alumina, zeolite, clay, ceramic, phosphate, clay and resin.

3. The process as defined by claim 2, wherein the acidic solid compound is selected from the group consisting of sulfonic acid resins, carboxylic resins, phosphoric resins, inorganic oxides, acidic clays, and zeolites.

4. The process as defined by claim 2, wherein the basic solid compound is selected from the group consisting of compounds carrying, at the surface, hydroxide functional groups or amine functional groups, carbonates, metal oxides, or basic clays.

5. The process as defined by claim 1, wherein the bifunctional catalyst comprises, as a second component, a metal, alkali metal or alkaline earth metal compound A.

6. The process as defined by claim 1, wherein the bifunctional catalyst comprises a metal compound based on Cr, Co, Ni, Cu, Rh, Pd, Ir, Pt and/or Au.

7. The process as defined by claim 5, wherein the compound A is present in proportions of between 0.001% and 30% by weight, with respect to the weight of the acidic or basic solid compound.

8. The process as defined by claim 1, wherein the catalyst comprises an acidic or basic solid compound on which the metal compound is supported at the surface.

9. The process as defined by claim 1, wherein the reaction medium comprises at least TDA and a solvent.

10. The process as defined by claim 1, wherein the reaction medium comprises from 30% to 70% by weight of TDA and from 30% to 70% by weight of DAA.

11. The process as defined by claim 1, wherein the reaction is carried out at a temperature of between 10° C. and 200° C.

12. The process as defined by claim 1, wherein the reaction is carried out at a pressure of between 1 bar and 100 bar.

13. The process as defined by claim 3, wherein the inorganic oxide is a sulfated zirconia.

14. The process as defined by claim 3, wherein the acidic clay is a montmorillonite.

15. The process as defined by claim 3, wherein the zeolite is H—ZSM5 or H—Y.

16. The process as defined by claim 4, wherein the metal oxide is a lanthanum phosphate or oxide.

17. The process as defined by claim 4, wherein the basic clay is a lamellar double hydroxides (LDH).

18. The process as defined by claim 7, wherein the compound A is present in a proportion of between 0.01% and 30% by weight.

\* \* \* \* \*